United States Patent [19]

Merritt et al.

[11] Patent Number: 6,040,442

[45] Date of Patent: *Mar. 21, 2000

[54] PROCESS FOR PREPARING 1,2,5-THIADIAZOLE CONTAINING ETHERS

[75] Inventors: Leander Merritt; John S. Ward, both of Indianapolis, Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 08/457,082

[22] Filed: Jun. 1, 1995

[51] Int. Cl.[7] ............... C07D 401/12; C07D 403/12; C07D 285/10; C07D 487/00

[52] U.S. Cl. ............... 540/461; 540/477; 540/520; 540/484; 540/584; 544/180; 544/235; 544/238; 544/239; 544/298; 544/367; 546/125; 546/137; 546/112; 546/208; 546/209; 546/141; 546/142; 546/268.7; 548/135

[58] Field of Search ............... 540/461, 450, 540/477, 520, 584, 484; 544/180, 235, 238, 239, 298, 367; 546/125, 209, 137, 141, 142, 112, 208, 268.7; 548/135

[56] References Cited

U.S. PATENT DOCUMENTS

| | | | |
|---|---|---|---|
| 4,555,521 | 11/1985 | Engel et al. | 514/362 |
| 5,605,908 | 2/1997 | Merritt et al. | 514/305 |
| 5,665,745 | 9/1997 | Alt et al. | 514/362 |

FOREIGN PATENT DOCUMENTS

| | | |
|---|---|---|
| 0 458 214 A1 | 5/1991 | European Pat. Off. |
| WO 94/14805 | 7/1994 | WIPO |

OTHER PUBLICATIONS

Ward, J.S. et al, J. Med. Chem. 1992, 35(22), pp. 4011–19.

"The Use of Diethyl Azodicarboxylate and Triphenylphosphine in Synthesis and Transformation of Natural Products," *Georg Theme Verlag*, pp. 1–27 (1981).

David L. Hughes, "The Mitsunobu Reaction," *Organic Reactions*, 42, pp. 335–381 (1992).

John S. Ward, et al., "Novel Functional $M_1$ Selective Muscarinic Agonists. 2. Synthesis and Structure–Activity Relationships of 3–Pyrazinyl–1,2,5,6–tetrahydro–1–methylpyridines. Construction of a Molecular Model for the $M_1$ Pharmacophore," *J. Med. Chem.* 35, pp. 4011–4019 (1992).

*Primary Examiner*—Alan L. Rotman
*Attorney, Agent, or Firm*—David M. Stemerick; MaCharri Vorndran-Jones

[57] ABSTRACT

The presently claimed process provides a method for preparing compounds of the formula $$\underset{3}{\begin{array}{c}OR^{11}\phantom{xx}OR^{12}\\ \diagup\phantom{xx}\diagup\\ N\diagdown\phantom{x}\diagup N\\ S\end{array}} \text{ and } \underset{1}{\begin{array}{c}GO\phantom{xx}R'\\ \diagup\phantom{xx}\diagup\\ N\diagdown\phantom{x}\diagup N\\ S\end{array}} \text{ using a}$$

phosphorous (III) compound and a diester of azodicarboxylate.

20 Claims, No Drawings

PROCESS FOR PREPARING 1,2,5-THIADIAZOLE CONTAINING ETHERS

FIELD OF THE INVENTION

The present invention relates to a process for making key intermediates useful for the synthesis of therapeutically active compounds.

BACKGROUND OF THE INVENTION

This invention provides a process for preparing key intermediates useful for the preparation of heterocyclic compounds. Such compounds include, but are not limited to azacyclic and azabicyclic compounds which are useful as stimulants of the cognitive function of the forebrain and hippocampus of mammals and especially in the treatment of Alzheimer's disease.

The process of this invention is particularly useful for preparing intermediates which are useful for making compounds of formula I'. The formula I' compounds exhibit muscarinic cholinergic agonist activity. Such compounds have the following structure:

$$G-(CH_2)_r-W\underset{N\diagdown S\diagup N}{\overset{R}{\diagup\!\!\!\diagdown}} \qquad (I')$$

wherein

W is oxygen or sulphur,

R is hydrogen, amino, halogen, $NHR^6NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), $-CF_3$, $-CN$, Y, phenyl or phenoxy wherein phenyl or phenoxy is optionally substituted with halogen, $-CN$, $C_{1-4}$-alkyl, $C_{1-4}$-alkoxy, $-OCF_3$, $-CH_3$, $-CONH_2$ or $-CSNH_2$; or R is phenyl or benzyloxycarbonyl, each of which is optionally substituted with halogen, $-CN$, $C_{1-4}$-alkyl, $C_{1-4}$-alkoxy, $-OCF_3$, $-CF_3$, $-CONH_2$ or $-CSNH_2$; or R is $-OR^5Y$, $-SR^5Y$, $OR^5-Z-Y$, $-SR^5ZY$, $-O-R^5-Z-R^4$ or $-S-R^5-Z-R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group; and G is selected from one of the following azacyclic or azabicyclic ring systems:

het-1 het-2 het-3 het-4 het-5 het-6 het-7 or G can optionally be substituted $C_3$–$C_8$ cycloalkyl or optionally substituted $C_{1-6}$-alkyl wherein the substitution is $-NR^6R^7$;

$R^6$ and $R^7$ independently are hydrogen, $C_{1-6}$-alkyl, $R^6$ and $R^7$ together with the nitrogen atom optionally form a 4- to 6-member ring;

$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with $-OH$, $-COR^{6'}$, $CH_2-OH$, halogen, $-NH_2$, carboxy, or phenyl;

$R^3$ is hydrogen, $C_{1-5}$-alkyl, $C_{2-5}$-alkenyl or $C_{2-5}$-alkynyl;

n is 0, 1 or 2;

m is 0,1 or 2;

p is 0, 1 or 2;

q is 1 or 2;

r is 0, 1 or 2;

....... is a single or double bond.

The present invention provides a process for making key intermediates which are useful for making heterocyclic compounds.

Further, the process may be completed via a convenient, one pot synthesis. Certain of the processes claimed herein provide a method for inverting the stereochemistry at the carbon bearing the hydroxyl group in the G substituent described supra. Such inverted stereochemistry can be important for the commercial development of pharmaceutically active compounds.

SUMMARY OF THE INVENTION

A process for preparing a compound of formula 1

$$GO\underset{N\diagdown S\diagup N}{\overset{R'}{\diagup\!\!\!\diagdown}} \qquad 1$$

wherein

R' is selected from the group consisting of hydrogen, halogen, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl);

R⁴ is selected from the group consisting of $C_{1-15}$-alkyl, $C_{2-15}$-alkenyl, $C_{2-15}$-alkynyl, each of which is optionally substituted with one or more independently selected from the group consisting of halogen(s), —CF$_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —OCF$_3$, or —CF$_3$; or R' is phenyl or benzyloxycarbonyl, each of which is optionally substituted with one or more independently selected from the group consisting of halogen, —CN, $C_{1-4}$-alkyl, $C_{1-4}$-alkoxy, —OCF$_3$, and —CF$_3$; or R' selected from the group consisting of —OR⁵Y, —SR⁵Y, OR⁵—Z—Y, —SR⁵ZY, —O—R⁵—Z—R⁴ and —S—R⁵—Z—R⁴;

Z is oxygen or sulphur,

R⁵ is selected from the group consisting of $C_{1-15}$-alkyl, $C_{2-15}$-alkenyl, and $C_{2-15}$-alkynyl;

Y is a 5 or 6 membered heterocyclic group;

R¹' is selected from the group consisting of phenyl, $C_{1-15}$-alkyl, $C_{2-5}$-alkenyl, $C_{2-5}$-alkynyl and (NR²')$_3$;

R²' and R³' are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl;

W is oxygen or sulphur;

G is selected from one of the following azacyclic or azabicyclic ring systems:

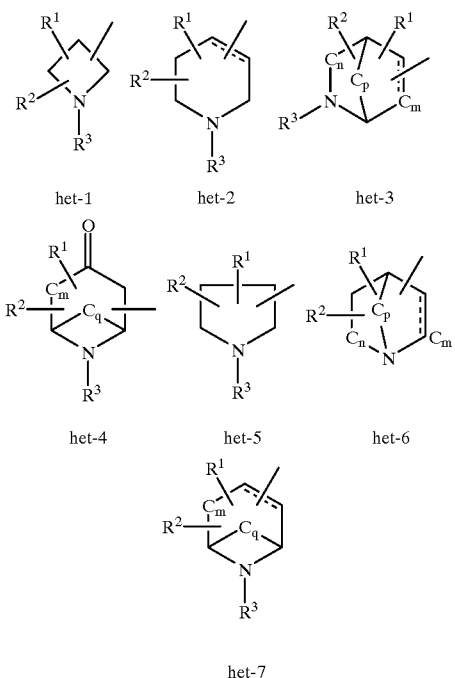

het-1    het-2    het-3 het-4    het-5    het-6 het-7 or G can optionally be substituted $C_3$–$C_8$ cycloalkyl or optionally substituted $C_{1-6}$-alkyl wherein the substitution is —NR⁶R⁷;

R⁶, and R⁷ independently are $C_{1-6}$-alkyl; or

R⁶ and R⁷ together with the nitrogen atom optionally form a 4- to 6-member ring;

R¹ and R² are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —COR⁶', halogen, and phenyl;

R⁶' is hydrogen or $C_1$–$C_3$ alkyl;

R³ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

........ is a single or double bond;

comprising contacting a compound of the formula 2

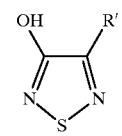

wherein R' is defined above; with a compound of the formula G—OH, a phosphorous (III) compound, and a diester of azodicarboxylate.

Additionally, this invention provides a process for preparing a compound of formula 3

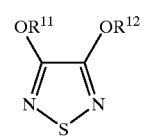

wherein

R¹¹ and R¹² are independently selected from the group consisting of hydrogen, R⁴, and G, provided that at least one of the group consisting of R¹¹ and R¹² is selected from the group consisting of R⁴ and G;

R⁴ is selected from the group consisting of $C_{1-15}$-alkyl, $C_{2-15}$-alkenyl, $C_{2-15}$-alkynyl, each of which is optionally substituted with one or more independently selected from the group consisting of halogen(s), —CF$_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —OCF$_3$, or —CF$_3$; or R⁵ is selected from the group consisting of $C_{1-15}$-alkyl, $C_{2-15}$-alkenyl, and $C_{2-15}$-alkynyl;

Y is a 5 or 6 membered heterocyclic group;

G is selected from one of the following azacyclic or azabicyclic ring systems:

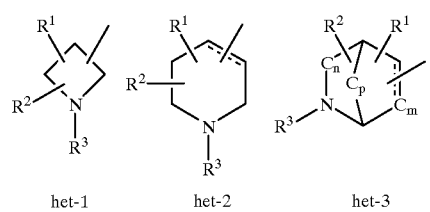

het-1    het-2    het-3

-continued

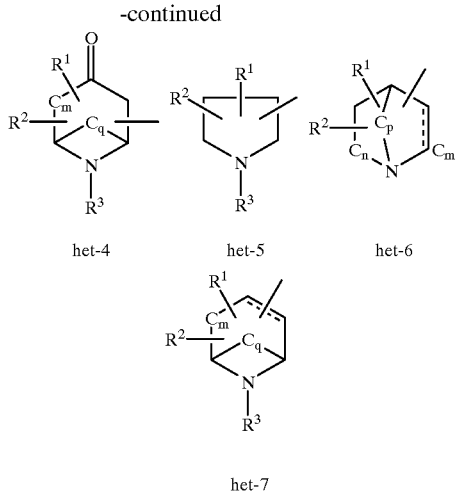

het-4   het-5   het-6 het-7 or G can optionally be substituted $C_3$–$C_8$ cycloalkyl or optionally substituted $C_{1-6}$-alkyl wherein the substitution is —$NR^6R^7$;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —$COR^{6'}$, halogen, and phenyl;

$R^{6'}$ is hydrogen or $C_1$–$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0,1 or 2;

p is 0,1 or 2;

q is 1 or 2;

r is 0, 1 or 2;

╌╌╌ is a single or double bond;

comprising contacting a compound of the formula 4

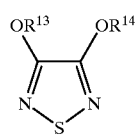

4

$R^{13}$ and $R^{14}$ are each independently selected from the group consisting of hydrogen, G, and $R^4$ provided that at least one selected from the group consisting of $R^{13}$ and $R^{14}$ is hydrogen;

with a phosphorous (III) compound and a diester of azodicarboxylate.

Further, this invention provides a process for making compounds of formula XIII

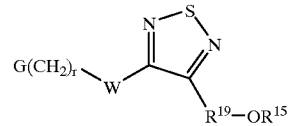

(XIII)

wherein W is oxygen or sulphur;

G is selected from one of the following azacyclic or azabicyclic ring systems:

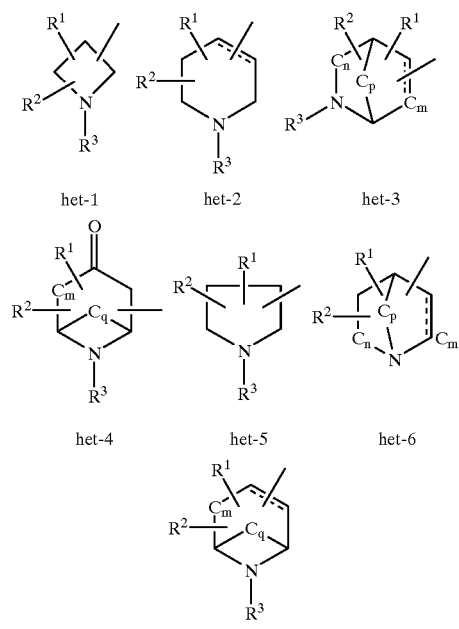

het-1   het-2   het-3 het-4   het-5   het-6 het-7 or G can optionally be substituted $C_3$–$C_8$ cycloalkyl or optionally substituted $C_{1-6}$-alkyl wherein the substitution is —$NR^6R^7$;

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —$COR^{6'}$, halogen, and phenyl;

$R^{6'}$ is hydrogen or $C_1$–$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

╌╌╌ is a single or double bond;

$R^6$ and $R^7$ independently are $C_{1-6}$-alkyl; or $R^6$ and $R^7$ together with the nitrogen atom optionally form a 4- to 6-member ring;

$R^{19}$ is selected from the group consisting of $R^7$, —$OR^7$, —$SR^7$, —$SOR^7$, —$SO_2R^7$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^7$ is $C_{1-15}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy; wherein phenyl or phenoxy is optionally substituted with one or more selected from the group consisting of halogen, —CN, $C_{1-4}$-alkyl, $C_{1-4}$-alkoxy, —$OCF_3$, and —$CF_3$;

provided that at least one alkyl atom of $R^{19}$ is substituted with a hydroxyl group or $R^{19}$ is selected from the group consisting of —$OR^8Y$, —$SR^8Y$, $OR^8$—Z—Y, —$SR^8ZY$, —O—$R^8$—Z—$R^7$ and —S—$R^8$—Z—$R^7$ provided that each —$OR^8Y$, $OR^8$—Z—Y, —$SR^8ZY$, —O—$R^8$—Z—$R^7$ and —S—$R^8$—Z—$R^7$ is substituted with an alkylhydroxyl substituent;

Y is a 5 or 6 membered heterocyclic group;

Z is oxygen or sulphur;

$R^8$ is selected from the group consisting of $C_{1-15}$-alkyl, $C_{2-15}$-alkenyl and $C_{2-15}$-alkynyl;

aryl and heteroaryl is optionally substituted with one or more independently selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$;

$R^{15}$ is selected from the group consisting of aryl and heteroaryl; wherein aryl or heteroaryl is optionally independently substituted with one or more selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$;

comprising contacting a compound of the formula (XIV)

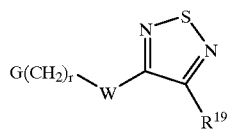

(XIV)

with a $R^{15}OH$ compound, a phosphorous (III) compound, and a diester of azodicarboxylate;

wherein $G(CH_2)_rW$, $R^{19}$, and $R^{15}$ are as defined supra.

DETAILED DESCRIPTION OF THE INVENTION

It is to be understood that the invention extends to each of the stereoisomeric forms of the compounds of the present invention as well as the pure diastereomeric, pure enatiomeric, and racemic forms of the compounds of this invention.

As used herein the term "treating" includes prophylaxis of a physical and/or mental condition or amelioration or elimination of the developed physical and/or mental condition once it has been established or alleviation of the characteristic symptoms of such condition.

As used herein with reference to the G substituent, the —$(CH_2)_r$—W-thiadiazole moiety can be attached at any carbon atom of the azacyclic or azabicyclic ring. Further, $R^1$ and $R^2$ of the G substituent may be present at any position, including the point of attachment of the —$(CH_2)_r$—W-thiadiazole moiety.

As used herein with reference to the G substituent, the phrase "$R^6$ and $R^7$ together with the nitrogen atom option-ally form a 4- to 6-member ring" means that $R^6$ and $R^7$ are each independently hydrogen, $C_1$–$C_6$ alkyl wherein the $R^6$ and $R^7$ groups may optionally join to form a 4- to 6-member ring including the nitrogen. For example, optionally joined groups include, but are not limited to:

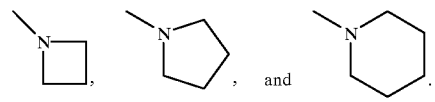

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

As used herein the phrase "one or more selected from" refers to from 1–3 substituents. The term shall further preferredly refer to from 1–2 substituents.

As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$. As used herein the term "alkaline metal hydroxide" shall include, but are not limited to $Li^+$, $K^+$, $Na^+$, $Cs^+$, and $Ca^{++}$. Preferred alkoxide metal include $Li^+$, $K^+$, and $Na^+$.

As used herein, the term "halogen" or the term "HAL" means Cl, Br, F, and I. Especially preferred halogens include Cl, Br, and I.

As used herein the phrase "one or more selected from" shall more preferredly refer to from 1–3 substituents. The term shall further preferredly refer to from 1–2 substituents.

As used herein the term "phosphorous(III) compound" has the art accepted meaning of the term. For example, the term includes, but is in no way limited to, triphenylphosphine, tri(p-toluyl) phosphine, tributyl phosphine, tri(p-dimethylaminiophenyl) phosphine, triethyl phosphine, and trimethyl phosphine. The artisan can choose other appropriate phosphorous(III) compounds using methods and literature references which are commonly available to the chemist artisan.

As used herein the term "diester of azodicarboxylate" has the art accepted meaning of the term. For example, the term includes, but is in no way limited to diethylazodicarboxylate, dimethylazodicarboxylate, diisopropylazodicarboxylate, and di-tertbutylazodicarboxylate. The skilled chemist can determine other appropriate diesters of azodicarboxylate using methods and literature readily available to the chemist artisan.

The terms "$C_1$–$C_{n'}$ alkyl" wherein n' can be from 2 through 15, as used herein, represent a branched or linear alkyl group having from one to the specified number of carbon atoms. Typical $C_1$–$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$–$C_{n'}$ alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl (—CH$_2$—CH=CH$_2$), 1,3-butadienyl, (—CH=CHCH=CH$_2$), 1-butenyl (—CH=CHCH$_2$CH$_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The terms "halogen($C_1$–$C_6$)alkyl" and "halogen($C_2$–$C_6$) alkenyl" refer to alkyl or alkenyl substituents having one or more independently selected halogen atoms attached at one or more available carbon atoms. These terms include, but are not limited to, chloromethyl, 1-bromoethyl, 2-bromoethyl, 1,1,1-trifluoroethyl, 1,1,2-trifluoroethyl, 1,2,2-trifluoroethyl, 2,2,2-trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, 1-chloroethylenyl, 2-chloroethylenyl, 5-fluoro-3-pentenyl, 3-chloro-2-bromo-5-hexenyl, 3-chloro-2-bromobutyl, trichloromethyl, 1,1-dichloroethyl, 1,2-dichloroethyl, 2,2-dichloroethyl, 1,4-dichlorobutyl, 3-bromopentyl, 1,3-dichlorobutyl, 1,1-dichloropropyl, and the like.

The term "$C_2$–$C_{10}$ alkanoyl" represents a group of the formula C(O) ($C_1$–$C_9$) alkyl. Typical $C_2$–$C_{10}$ alkanoyl groups include acetyl, propanoyl, butanoyl, and the like.

The term "($C_1$–$C_6$ alkyl) amino" refers to a monoalkylamino groups. Examples of such groups are methylamino, ethylamino, iso-propylamino, n-propylamino, (n-propyl) amino, (iso-propyl)amino, n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted($C_5$–$C_{n'}$) cycloalkyl" refers to a cycloalkyl groups as described supra wherein the cycloalkyl group may be substituted with from one to four substituents independently selected from the group consisting of hydrogen, $C_1$–$C_6$ alkyl, NO$_2$, halogen, halogen($C_1$–$C_6$) alkyl, halogen($C_2$–$C_6$)alkenyl, $C_2$–$C_6$ alkenyl, CO$_2$R$^{20}$, ($C_1$–$C_6$ alkyl) amino, —SR$^{20}$, and OR$^{20}$; wherein R$^{20}$ is selected from the group consisting of $C_{1-15}$-alkyl, $C_{2-15}$-alkenyl, $C_{2-15}$-alkynyl.

The term "$C_3$–$C_8$ cycloalkyl-($C_1$–$C_3$)alkyl" represents an alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

The term "substituted ($C_5$–$C_8$) cycloalkenyl" refers to a cycloalkenyl group as described supra, wherein the cycloalkenyl group may be substituted with from one to four substituents independently selected from the group consist-ing of hydrogen, $C_1$–$C_6$ alkyl, NO$_2$, halogen, halogen ($C_1$–$C_6$)alkyl, halogen($C_2$–$C_6$)alkenyl, $C_2$–$C_6$ alkenyl, COR$^{20}$, $C_2$–$C_{10}$ alkanoyl, $C_7$–$C_{16}$ arylalkyl, CO$_2$R$^{20}$, ($C_1$–$C_6$ alkyl) amino, —SR$^{20}$, and —OR$^{20}$; wherein R$^{20}$ is selected from the group consisting of $C_{1-15}$- alkyl, $C_{2-15}$-alkenyl, and $C_{2-15}$-alkynyl.

The term "$C_5$–$C_8$ cycloalkenyl-($C_1$–$C_3$)alkyl" represents a $C_1$–$C_3$ alkyl group substituted at a terminal carbon with a $C_5$–$C_8$ cycloalkenyl group.

As used herein, the phrase "5 or 6 membered heterocyclic group" means a group containing from one to four N, O or S atom(s) or a combination thereof, which heterocyclic group is optionally substituted at carbon or nitrogen atom(s) with $C_{1-6}$-alkyl, —CF$_3$, phenyl, benzyl or thienyl, or a carbon atom in the heterocyclic group together with an oxygen atom form a carbonyl group, or which heterocyclic group is optionally fused with a phenyl group. The phase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

The term "heteroaryl" refers to a group which is a 5 or 6 membered heterocycle containing one to four N, O, or S atoms or a combination thereof.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl" refers to any aryl group which is attached to the parent moiety via the alkyl group.

As used herein the phrase "one or more selected from" refers more preferredly to from 1–3 substituents. The term further preferredly refers to from 1–2 substituents.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

The starting materials for the illustrated processes are commercially available or may be prepared using methods known to the skilled artisan.

Certain compounds of this invention may more preferredly be prepared by a process using a hydroxyalkylamine (G—OH) wherein G has the meaning defined supra. in the presence of a phosphorous(III) compound, for example, but not in any way limited to triphenylphosphine, and a diester of azodicarboxylate, for example, but not in any way limited to diethylazodicarboxylate to give the 1,2,5-thiadiazoyloxyalkylamine as illustrated by Scheme IV.

Scheme IV

The G groups are as defined supra. The R' is selected from the group consisting of hydrogen, halogen, $NR^6R^7$, $R^4$, $-OR^4$, $-SR^4$, $-SOR^4$, $-SO_2R^4$, $C_{3-10}$-cycloalkyl, $C_{4-12}$-(cycloalkylalkyl), $-Z-C_{3-10}$-cycloalkyl and $-Z-C_{4-12}$-(cycloalkylalkyl);

$R^4$ is selected from the group consisting of $C_{1-15}$-alkyl, $C_{2-15}$-alkenyl, $C_{2-15}$-alkynyl, each of which is optionally substituted with one or more independently selected from the group consisting of halogen(s), $-CF_3$, $-CN$, Y, phenyl and phenoxy wherein phenyl or phenoxy is optionally substituted with one or more independently selected from the group consisting of halogen, $-CN$, $C_{1-4}$-alkyl, $C_{1-4}$-alkoxy, $-OCF_3$, or $-CF_3$; or R' is phenyl or benzyloxycarbonyl, each of which is optionally substituted with one or more independently selected from the group consisting of halogen, $-CN$, $C_{1-4}$-alkyl, $C_{1-4}$-alkoxy, $-OCF_3$, and $-CF_3$; or R' selected from the group consisting of $-OR^5Y$, $-SR^5Y$, $OR^5-Z-Y$, $-SR^5ZY$, $-O-R^5-Z-R^4$ and $-S-R^5-Z-R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5 or 6 membered heterocyclic group;

$R^{1'}$ is selected from the group consisting of phenyl, $C_{1-15}$-alkyl, $C_{2-5}$-alkenyl, $C_{2-5}$-alkynyl and $(NR^{2'})_3$;

$R^{2'}$ and $R^{3'}$ are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl;

W is oxygen or sulphur;

G is selected from one of the following azacyclic or azabicyclic ring systems:

het-1    het-2    het-3 het-4    het-5    het-6 het-7 or G can optionally be substituted $C_3$–$C_8$ cycloalkyl or optionally substituted $C_{1-6}$-alkyl wherein the substitution is $-NR^6R^7$;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of $-COR^{6'}$, halogen, and phenyl;

$R^{6'}$ is hydrogen or $C_1$–$C_3$ alkyl;

$R^3$ is selected from the group consisting of $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

┈┈ is a single or double bond;

Preferred $R^{1'}$ groups include phenyl, $C_{1-15}$-alkyl, and $(NR^{2'})_3$. The process of Scheme IV is particularly advantageous because the process provides a method for inverting the stereochemistry at the carbon bearing the hydroxyl group in G.

Another new process illustrated by Scheme V, involves the sequential reaction of 3,4-dihydroxy-1,2,5-thiadiazole with G—OH wherein G is defined as defined supra. in the presence of a phosphorous(III) compound and a diester of azodicarboxylate to give an unisolated hydroxy-1,2,5- thiadiazole ether I" followed by reaction of I" with R⁴OH where R⁴ is defined as supra. with phosphorous(III) compounds and a diester of azodicarboxylate to give the diethers of 3,4-dihydroxy-1,2,5-thiadiazole which are useful as muscarinic agonists and antagonists. (See, *Org. Prep. & Procedures* 1969, 1, 255–258). The substituents illustrated in Scheme V are as defined supra.

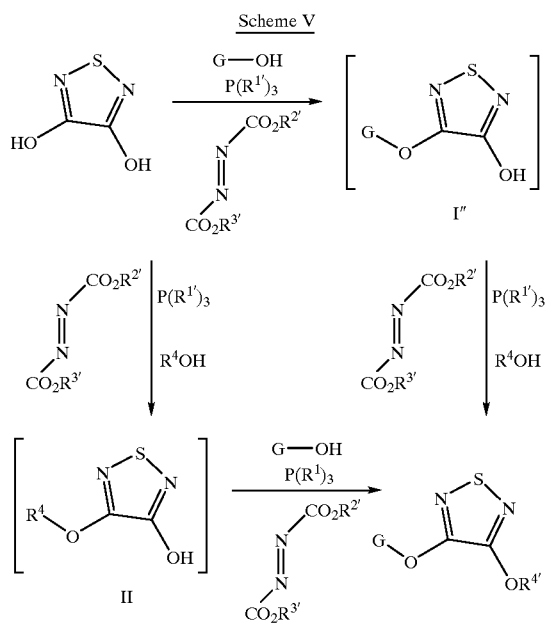

Alternatively, the order of addition of the alcohols may be reversed as shown above to give unisolated hydroxy-1,2,5-thiadiazole ether II which is subsequently converted to the same final muscarinic active compound.

The process illustrated by Scheme VI emcompassed the reaction of a phenol or hydroxyheteroaryl compound with compound III in the presence of a phosphorous(III) compound and a diester of azodicarboxylate to give compound IV.

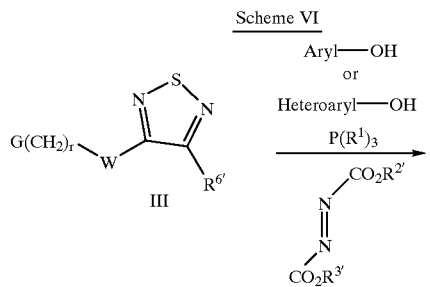

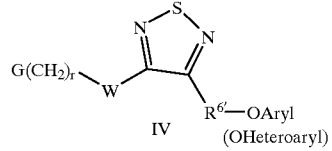

In compound III, G(CH₂)ᵣW is as defined supra. and $R^{6'}$ is selected from the group consisting of $R^7$, —$OR^7$, —$SR^7$, —$SOR^7$, —$SO_2R^7$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^7$ is $C_{1-15}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy; wherein phenyl or phenoxy is optionally substituted with one or more selected from the group consisting of halogen, —CN, $C_{1-4}$-alkyl, $C_{1-4}$-alkoxy, —$OCF_3$, and —$CF_3$;

provided that at least one alkyl atom of $R^{6'}$ is substituted with a hydroxyl group or $R^{6'}$ is a substituent selected from the group consisting of —$OR^8Y$, —$SR^8Y$, $OR^8$—Z—Y, —$SR^8ZY$, —O—$R^8$—Z—$R^7$ and —S—$R^8$—Z—$R^7$ wherein each —$OR^8Y$, —$SR^8Y$, $OR^8$—Z—Y, —$SR^8ZY$, —O—$R^8$—Z—$R^7$ and —S—$R^8$—Z—$R^7$ is substituted with a alkylhydroxyl;

Y is a 5 or 6 membered heterocyclic group;

Z is oxygen or sulphur;

$R^8$ is $C_{1-15}$-alkyl, $C_{2-15}$-alkenyl, $C_{2-15}$-alkynyl;

aryl and heteroaryl is optionally substituted with one or more independently selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$; heteroaryl group is a 5 or 6 membered heterocycle containing one to four N, O, or S atoms or a combination thereof.

The compounds prepared using the process of this invention can be used for making pharmaceutically active compounds as illustrated by the following Schemes II, and III.

Compounds of Formula I may be prepared using the process illustrated in the following Scheme II

Scheme II

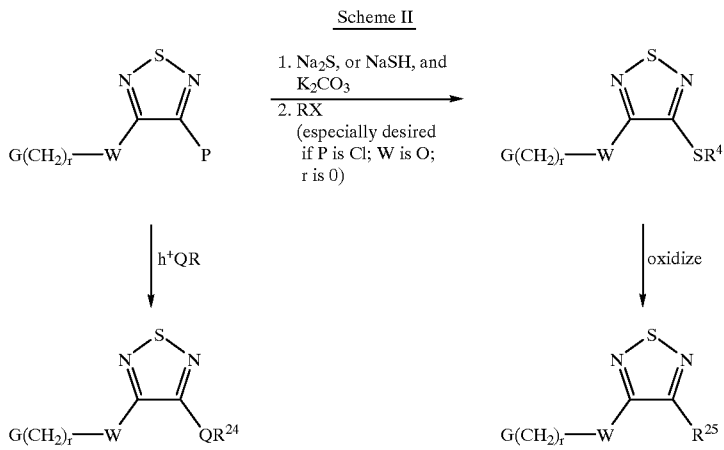

As used in Scheme II, Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme III.

Scheme III

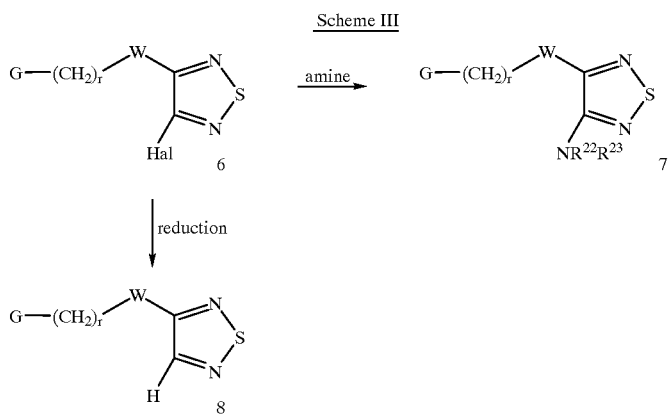

As used in Scheme III, Hal, W, r, and G are as defined supra. As used in Scheme III, $R^{22}$ and $R^{23}$ are independently selected from the group consisting of hydrogen, $R^6$ and $R^7$.

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

The intermediates and processes of the present invention are useful for preparing compounds having beneficial muscarinic receptor activity.

The following example is provided for illustrative purposes only, and is not intended to limit the scope of the claimed invention in any way.

PREPARATION 1

3-Chloro-4-(1-butylthio)-1,2,5-thiadiazole

Cyanogen (36 g, 0.69 mol) was bubbled into ether (250 mL) maintained at −10° C. To the solution was added dropwise diethylamine (3 mL) followed by dropwise addition of 1-butylthiol (47 mL, 0.64 mol) at such a rate that the temperature did not exceed −5° C. The reaction was maintained below 0° C. for 5 h then stirred at ambient overnight. Ether was distilled from the reaction until the pot temperature reached 50° C. The reaction was cooled to ambient and then added dropwise to a solution of sulfur monochloride (55 mL, 0.688 mol) in DMF (50 mL) that was cooled to 5° C. Cooling was removed and reaction was stirred overnight. The reaction was cooled in an ice-water bath and excess sulfur monochloride destroyed by careful addition of $H_2O$ while maintaining the temperature below 40° C. The liquid was decanted from the semi-solid sulfur precipitant and the sulfur residue triturated with hexane. The aqueous fraction was extracted with hexane (3 X) and the combined extracts and triturants were washed with $H_2O$, aqueous $NaHCO_3$, brine, dried, and the solvent evaporated. The residue was distilled at 2 mm Hg to give a yellow liquid (24.6 g), b.p. 105–110° C. (Compound 1).

PREPARATION 2

3-Chloro-4-ethoxy-1,2,5-thiadiazole

A solution of ethanol (60 mL, 1.02 mol) and triethylamine (1.5 mL) was cooled to −8° C. and cyanogen (59 g, 1.13 mol) was slowly bubbled through the solution while maintaining the temperature below 2° C. The reaction was then added dropwise to a solution of DMF (275 mL) and sulfur monochloride (225 mL, 2.81 mol) that was cooled to 5° C. while maintaining the temperature of the DMF solution below 10° C. Cooling was removed and the reaction was stirred over night. The reaction was cooled in an ice-water bath and the excess sulfur monochloride destroyed by dropwise addition of $H_2O$ such that the temperature did not exceed 30° C. Additional $H_2O$ (400 mL) was added and the reaction internally steam distilled until the distillate was almost homogeneous. The distillate was extracted with hexane (3 X) and the combined extracts washed with H2O, aqueous $NaHCO_3$, brine, dried, and the solvent carefully evaporated. The liquid residue was distilled at 21 mm Hg to give a clear liquid (154.3 g), b.p. 88–93° C. (Compound 93).

EXAMPLE 1

(±)-3-(2-Methylthioethyl)-4-(1-azabicyclo[2.2.2]octyl-3-oxy)-1,2,5-thiadiazole

A solution of 3-(2-methylthioethyl)-4-hydroxy-1,2,5-thiadiazole (0.45 g) and triphenylphosphine (0.7 g) was cooled in ice-water as diethyldiazodicarboxylate (0.4 mL) was added dropwise. After addition, (±)-1-azabicyclo[2.2.2]octan-3-ol (0.33 g) was added, cooling removed, and reaction stirred for 1 hour. The solvent was evaporated, residue suspended in water, the mixture acidified and washed with ether. The aqueous solution was made basic and extracted with EtOAc. The extracts were dried, the solvent evaporated, the residue purified by radial chromatography eluting with 10%-EtOH-1%—$NH_4OH$—$CHCl_3$, and the product converted to a HCl salt. Recrystallization from acetone gave 0.6 g white crystals, m.p. 177–178° C. (Compound 99).

The following compounds were synthesized in substantially the same manner as Compound 99.

EXAMPLE 2

(±)-3-(1-azabicyclo[2.2.2]octyl-3-oxy)-1,2,5-thiadiazole

A sample of 3-Hydroxy-1,2,5-thiadiazole (0.28 g), triphenylphospine (0.7 g), diethyldiazodicarboxylate (0.4 mL), and (±)-1-azabicyclo[2.2.2]octan-3-ol (0.33 g) gave the hydrochloride salt of (±)-3-(1-azabicycle[2.2.2]octyl-3-oxy)-1,2,5-thiadiazole, m.p. 240° C. dec. (0.36 g). (Compound 100).

EXAMPLE 3

(±)-3-Hexyl-4-(1-azabicyclo[2.2.2]octyl-3-oxy)-1,2,5-thiadiazole

A sample of 3-Hexyl-4-Hydroxy-1,2,5-thiadiazole (0.93 g), triphenylphospine (1.31 g), diethyldiazodicarboxylate (0.8 mL), and (±)-1-azabicyclo[2.2.2]octan-3-ol (0.64 g) gave the hydrochloride salt of (±)-3-hexyl-4-(1-azabicyclo[2.2.2]octyl-3-oxy)-1,2,5-thiadiazole, m.p. 163–164° C dec. (1.11 g). (Compound 101).

EXAMPLE 4

(±)Exo-3-Butylthio-4-(1-azabicyclo[2.2.1]heptyl-3-oxy)-1,2,5-thiadiazole

A solution of triphenylphosphine (0.7 g) and Compound 300 (0.5 g) in THF (20 mL) was cooled in ice-water. Diethyl diazodicarboxylate (0.4 mL) was added dropwise followed by addition of (±)endo-3-hydroxy-1-azabicyclo[2.2.1]heptane (0.29 g). Cooling was removed and after 1 h the solvent was evaporated. The residue was suspended in cold water, acidified, and extracted with ether. The aqueous fraction was made basic and extracted with EtOAc. The extracts were dried, the solvent evaporated, and the residue purified by radial chromatography eluting with 5%-EtOH-0.5% $NH_4OH$—$CHCl_3$ to give a clear oil. The HCl salt crystallized from EtOAc as white crystals (0.44 g), m.p. 147–148° C. (Compound 301).

EXAMPLE 5

(±)exo-3-(1-Azabicyclo[2.2.1]heptyl-3-oxy)-1,2,5-thiadiazole

Prepared in the same manner as Compound 301. (±)Exo-3-(1-azabicyclo[2.2.1]heptyl-3-oxy)-1,2,5-thiadiazole was obtained from 3-hydroxy-1,2,5-thiadiazole (0.14 g), triphenylphosphine (0.35 g), diethyldiazodicarboxylate (0.21 mL) and (±)-endo-1-azabicyclo[2.2.1]heptane-3-ol (0.15 g) as a hydrochloride salt (0.096 g), m.p. 223° C. dec. (Compound 302).

EXAMPLE 6

3-Butylthio-4-hydroxy-1,2,5-thiadiazole

A solution of Compound 1 (20.9 g), DMSO (20 mL) and 2N NaOH (205 mL) was heated to reflux overnight. The solution was cooled to 15° C. and concentrated HCl was added until the pH was 1. The solid was collected, washed with water, and dried to give a solid (17.68 g). Recrystallization from heptane gave white crystals, m.p. 72–72.5° C. (Compound 300).

EXAMPLE 7

3Ethoxy-4-hydroxy-1,2,5-thiadiazole

A mixture of Compound 93 (8.2 g), 2N NaOH (100 mL), and DMSO (10 mL) was heated to reflux over night. The reaction was cooled and extracted with ether. The aqueous fraction was acidified with conc. HCl and cooled 30 min in ice-water. The solid was collected from the resulting mixture by filtration and washed with a small amount of cold water to give white crystals (4.4 g). Recrystallization from heptane gave white flakes, m.p. 104.5–105.5° C. (Compound 303).

EXAMPLE 8

3-Propylthio-4-hydroxy-1,2,5-thiadiazole

A mixture of 3-chloro-4-propylthio-1,2,5-thiadiazole (10 g), 2 N NaOH (100 mL), and DMSO (10 mL) was heated to reflux for 24 h. The solution was cooled and extracted with ether. The aqueous fraction was acidified with conc. HCl and cooled in ice-water for 3 h. The resulting solid was collected, washed with a small amount of cold water to give a white solid (8.15 g). Recrystallization from heptane gave white crystals, m.p. 84–85° C. (Compound 304).

We claim:
1. A process for preparing a compound of formula 1

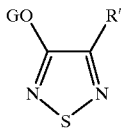

wherein $R^1$ is hydrogen, halogen, $NR^6R^7$, $R^4$, —$OR^4$, —$SR^4$, $SOR^4$, —$SO_2R^4$, $C_{3-10}$-cycloalkyl, $C_{4-12}$-(cycloalkylalkyl), —Z—$C_{3-10}$-cycloalkyl, —Z—$C_{4-12}$-(cycloalkylalkyl), —$OR^5Y$, —$SR^5Y$, —$OR^5ZY$, —$SR^5ZY$, —$OR^5ZR^4$, —$SR^5ZR^4$, phenyl or benzyloxycarbonyl, or phenyl or benzyloxycarbonyl substituted with one or more substituents independently selected from halogen, —CN, $C_{1-4}$-alkyl, $C_{1-4}$-alkoxy, —$OCF_3$, or —$CF_3$;

$R^4$ is $C_{1-15}$-alkyl, $C_{2-15}$-alkenyl, or $C_{2-15}$-alkynyl, each of which is optionally substituted with one or more substituents independently selected from halo, —$CF_3$, —CN, Y, phenyl or phenoxy, or phenyl or phenoxy substituted with one or more substituents independently selected from halo, —CN, $C_{1-4}$-alkyl, $C_{1-4}$-alkoxy, —$OCF_3$, or —$CF_3$;

Z is oxygen or sulphur;

$R^5$ is $C_{1-15}$-alkylene, $C_{2-15}$-alkenylene, or $C_{2-15}$-alkynylene;

Y is a 5 or 6 membered heterocyclic group;

$R^6$ and $R^7$ independently are $C_{1-6}$-alkyl; or $R^6$ and $R^7$ together with the nitrogen atom from a 4- to 6-membered ring;

G is an azacyclic or azabicyclic ring system selected from:

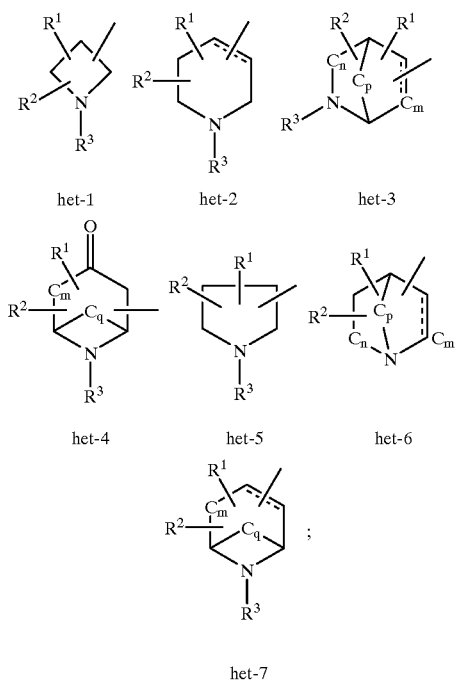

$R^1$ and $R^2$, independently, are hydrogen, $C_{1-15}$-alkyl, $C_{2-5}$-alkenyl, $C_{2-5}$-alkynyl, $C_{1-10}$-alkoxy, or $C_{1-5}$-alkyl substituted with one or more substituents independently selected from —$COR^{6'}$, halo or phenyl;

$R^{6'}$ is hydrogen or $C_1$–$C_3$ alkyl;

$R^3$ is $C_{1-5}$-alkyl, $C_{2-5}$-alkenyl or $C_{2-5}$-alkynyl;

m, n, p and p, independently, are 0, 1 or 2;

q is 1 or 2; and

--- is a single or double bond;

comprising contacting a compound of formula 2

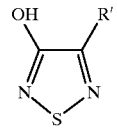

wherein R' is as defined supra; with a compound of the formula G—OH, a phosphorous(III) compound, and a diester of azodicarboxylate.

2. A process of claim 1 wherein the phosphorous(III) compound has the formula $P(R^{1'})_3$, wherein $R^{1'}$ is phenyl, $C_{1-15}$-alkyl, $C_{2-5}$-alkenyl, $C_{2-5}$-alkynyl, or $N(R^{2'})_2$; and $R^{2'}$ is hydrogen, $C_{1-15}$-alkyl, $C_{2-5}$-alkenyl, $C_{2-5}$-alkynyl, or $C_{1-5}$-alkyl having one or more halo or phenyl substituents.

3. A process of claim 1 wherein the diester of azodicarboxylate has the formula

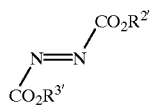

$R^{2'}$ and $R^{3'}$, independently, are hydrogen, $C_{1-15}$-alkyl, $C_{2-5}$-alkenyl, $C_{2-5}$-alkynyl, or $C_{1-5}$-alkyl having one or more halo or phenyl substituents.

4. A process of claim 2 wherein the diester of azodicarboxylate has the formula

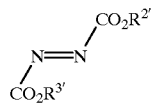

$R^{2'}$ and $R^{3'}$, independently, are hydrogen, $C_{1-15}$-alkyl, $C_{2-5}$-alkenyl, $C_{2-5}$-alkynyl, or $C_{1-5}$-alkyl having one or more halogen or phenyl substituents.

5. A process for preparing a compound of formula 3a

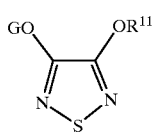

wherein $R^{11}$ is hydrogen or $R^4$;

$R^4$ is $C_{1-15}$-alkyl, $C_{2-15}$-alkenyl, or $C_{2-15}$-alkynyl, each of which is optionally substituted with one or more substituents independently selected from halo, —$CF_3$, —CN, Y, phenyl or phenoxy, or phenyl or phenoxy substituted with one or more substituents independently selected from halo, —CN, $C_{1-4}$-alkyl, $C_{1-4}$-alkoxy, —$OCF_3$, or —$CF_3$;

Y is a 5 or 6 membered heterocyclic group;

G is an azacyclic or azabicyclic ring system selected from

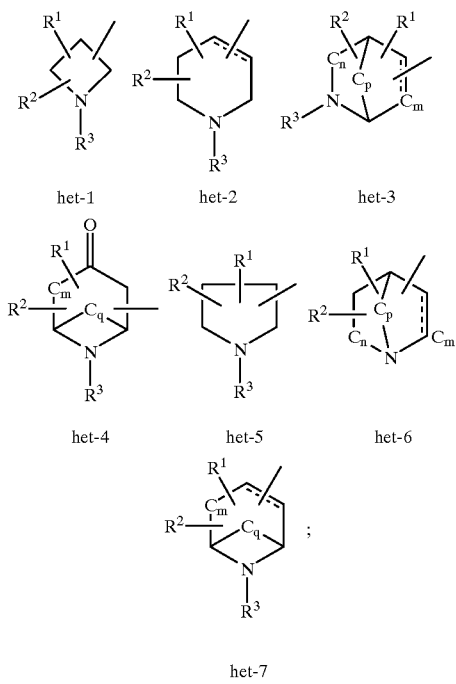

$R^6$ and $R^7$ independently are $C_{1-6}$-alkyl; or $R^6$ and $R^7$ together with the nitrogen atom form a 4- to 6-membered ring;

$R^1$ and $R^2$, independently, are hydrogen, $C_{1-15}$-alkyl, $C_{2-5}$-alkenyl, $C_{2-5}$-alkynyl, $C_{1-10}$-alkoxy, or $C_{1-5}$-alkyl substituted with one or more substituents independently selected from —$COR^{6'}$, halo or phenyl;

$R^{6'}$ is hydrogen or $C_1$–$C_3$ alkyl;

$R^3$ is $C_{1-5}$-alkyl, $C_{2-5}$-alkenyl or $C_{2-5}$-alkynyl;

m, n, p and p, independently, are 0, 1 or 2;

q is 1 or 2; and

--- is a single or double bond;

comprising contacting a compound of formula 4

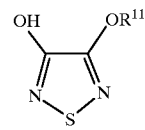

with a phosphorous(III) compound and a diester of azodicarboxylate.

6. A process of claim 5 wherein the phosphorous (III) compound has the formula $P(R^{1'a})_3$, wherein $R^{1'a}$ is phenyl, $C_{1-15}$-alkyl, $C_{2-5}$-alkenyl, $C_{2-5}$-alkynyl, $C_{1-10}$-alkoxy, or $C_{1-5}$-alkyl having one or more —$COR^{6'}$, halo, or phenyl substituents.

7. A process of claim 5 wherein the diester of azodicarboxylate has the formula

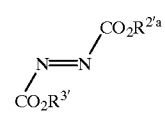

$R^{2'a}$ and $R^{3'a}$, independently, are hydrogen, $C_{1-15}$-alkyl, $C_{2-5}$-alkenyl, $C_{2-5}$-alkynyl, $C_{1-10}$-alkoxy, or $C_{1-5}$-alkyl having one or more —$COR^{6'}$, halo or phenyl substituents.

8. A process of claim 6 wherein the diester of azodicarboxylate has the formula

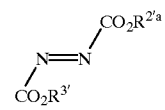

wherein $R^{2'a}$ and $R^{3'a}$, independently, are hydrogen, $C_{1-15}$-alkyl, $C_{2-5}$-alkenyl, $C_{2-5}$-alkynyl, $C_{1-10}$-alkoxy, or $C_{1-5}$-alkyl having one or more —$COR^{6'}$, halo or phenyl substituents.

9. A process of claim 3 wherein the diester of azodicarboxylate is diethyl azodicarboxylate.

10. A process of claim 4 wherein the phosphorous (III) compound is triphenylphosphine.

11. A process of claim 4 wherein G is unsaturated.

12. A process of claim 1 wherein R' is $R^4$, and $R^4$ is $C_{1-6}$-alkyl.

13. A process of claim 7 wherein the diester of azodicarboxylate is diethyl azodicarboxylate.

14. A process of claim 8 wherein the phosphorous (III) compound is triphenylphosphine.

15. A process of claim 8 wherein G is unsaturated.

16. A process of claim 5 wherein R' is $R^4$, and $R^4$ is $C_1$–$C_6$ alkyl.

17. A process of claim 1 wherein a stereocenter is inverted.

18. A process of claim 5 wherein a stereocenter is inverted.

19. A process of claim 7 wherein the phosphorous (III) compound is triphenylphosphine; the diester of azodicarboxylate is diethyl azodicarboxylate; and G is an azacyclic or azabicyclic ring.

20. A process of making a compound of formula XIII

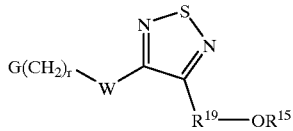

(XIII)

wherein

W is oxygen or sulphur;

G is an azacyclic or azabicyclic ring system selected from:

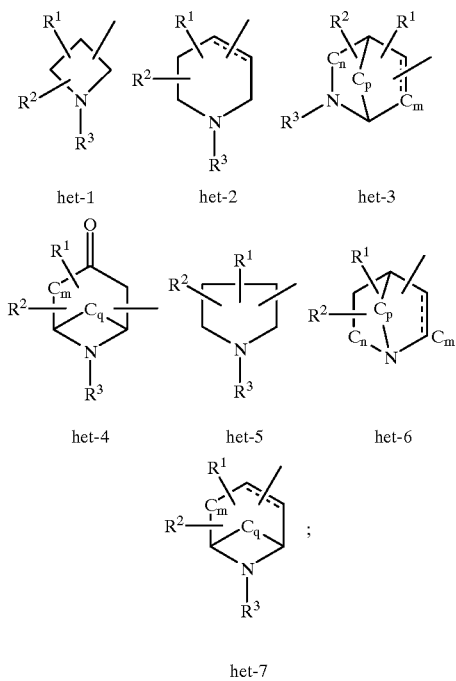

$R^1$ and $R^2$, independently, are hydrogen, $C_{1-15}$-alkyl, $C_{2-5}$-alkenyl, $C_{2-5}$-alkynyl, $C_{1-10}$-alkoxy, or $C_{1-5}$-alkyl substituted with one or more substituents independently selected from $—COR^{6'}$, halo or phenyl;

$R^{6'}$ is hydrogen or $C_1$–$C_3$ alkyl;

$R^3$ is $C_{1-5}$-alkyl, $C_{2-5}$-alkenyl or $C_{2-5}$-alkynyl;

m, n, p and r, independently, are 0, 1 or 2;

q is 1 or 2;

- - - is a single or double bond;

$R^6$ and $R^7$ independently are $C_{1-6}$-alkyl; or $R^6$ and $R^7$ together with the nitrogen atom form a 4- to 6-membered ring;

$R^{19}$ is $—R^4—$, $—OR^4—$, $—SR^4—$, $—SOR^4—$, $C_{3-10}$-cycloalkylene, $C_{4-12}$-(cycloalkylalkylene), $—Z—C_{3-10}$-cycloalkylene, $—Z—C_{4-12}$-(cycloalkylalkylene), $—OR^5Y—$, $—SR^5Y—$, $—OR^5ZY—$, $—SR^5ZY—$, $—OR^5ZR^4—$ or $—SR^5ZR^4—$;

$R^4$ is $C_{1-15}$-alkyl, $C_{2-15}$-alkenyl, or $C_{2-15}$-alkynyl, each of which is optionally substituted with one or more substituents independently selected from halo, $—CF_3$, $—CN$, Y, phenyl or phenoxy, or phenyl or phenoxy substituted with one or more substituents independently selected from halo, $—CN$, $C_{1-4}$-alkyl, $C_{1-4}$-alkoxy, $—OCF_3$, or $—CF_3$;

Y is a 5 or 6 membered heterocyclic group

Z is oxygen or sulphur;

$R^5$ is $C_{1-15}$-alkylene, $C_{2-15}$-alkenylene or $C_{2-15}$-alkynylene;

$R^{15}$ is aryl or heteroaryl, or aryl or heteroaryl substituted with one or more substituents independently selected from halo, $—CN$, $C_{1-4}$-alkyl, $C_{1-4}$-alkoxy, $C_{1-4}$-alkylthio, $C_{1-4}$-alkylsulfonyl, $C_{1-4}$-alkylsulfoxide, $—OCF_3$, $NO_2$, $N(R^7)_2$, and $—CF_3$; comprising 1) contacting a compound of formula XIV

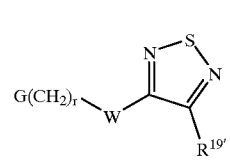

(XIV)

wherein G, r, and W, are as defined supra, and $R^{19'}$ is a hydroxyl-substituted group wherein the group is selected from $R^4$, $—OR^4$, $—SR^4$, $—SOR^4$, $—SO_2R^4$, $C_{3-10}$-cycloalkyl, $C_{4-12}$-(cycloalkylalkyl), $—Z—C_{3-10}$-cycloalkyl, $—Z—C_{4-12}$-(cycloalkylalkyl), and the hydroxyl substituent is located on the alkyl component of the $R^{19'}$ group;

or $R^{19'}$ is a hydroxyalkyl-substituted group wherein the group is selected from $—OR^5Y$, $—SR^5Y$, $—OR^5ZY$, $—SR^5ZY$, $—OR^5ZR^4$ or $—SR^5ZR^4$; with an $R^{15}OH$ compound, a phosphorous(III) compound, and a diester of azodicarboxylate; or 2) contacting a compound of formula XIVa

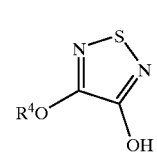

(XIVa)

wherein $R^4$ is as defined supra, with a GOH compound, a phosphorous(III) compound, and a diester of azodicarboxylate.

* * * * *